(12) United States Patent
Kluckner et al.

(10) Patent No.: US 10,816,538 B2
(45) Date of Patent: Oct. 27, 2020

(54) METHODS AND APPARATUS FOR DETECTING AN INTERFERENT IN A SPECIMEN

(71) Applicant: Siemens Healthcare Diagnostics Inc., Tarrytown, NY (US)

(72) Inventors: Stefan Kluckner, Berlin (DE); Yao-Jen Chang, Princeton, NJ (US); Terrence Chen, Princeton, NJ (US); Benjamin S. Pollack, Jersey City, NJ (US); Patrick Wissmann, Munich (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 7 days.

(21) Appl. No.: 16/072,423

(22) PCT Filed: Jan. 24, 2017

(86) PCT No.: PCT/US2017/014775
§ 371 (c)(1),
(2) Date: Jul. 24, 2018

(87) PCT Pub. No.: WO2017/132169
PCT Pub. Date: Aug. 3, 2017

(65) Prior Publication Data
US 2018/0372715 A1    Dec. 27, 2018

Related U.S. Application Data
(60) Provisional application No. 62/288,375, filed on Jan. 28, 2016.

(51) Int. Cl.
*G01N 33/49* (2006.01)
*G01N 21/25* (2006.01)
(Continued)

(52) U.S. Cl.
CPC ......... *G01N 33/491* (2013.01); *G01N 21/251* (2013.01); *G01N 21/31* (2013.01);
(Continued)

(58) Field of Classification Search
CPC .... G01N 33/491; G01N 21/31; G01N 21/251; G01N 21/314; G01N 33/492;
(Continued)

(56) References Cited

U.S. PATENT DOCUMENTS 7,126,630 B1    10/2006   Lee et al.
7,611,839 B2    11/2009   Twine et al.
(Continued)

FOREIGN PATENT DOCUMENTS

JP    2005 345370 A    12/2005
WO    02/068932 A1    9/2002
(Continued)

OTHER PUBLICATIONS

Extended EP Search Report dated Nov. 14, 2018 of corresponding European Application No. 17744780.2, 5 Pages.
(Continued)

*Primary Examiner* — Michael P LaPage

(57) ABSTRACT

A model-based method of inspecting a specimen for presence of an interferent (H, I, and/or L). The method includes capturing images of the specimen at multiple different exposures times and at multiple spectra having different nominal wavelengths, selection of optimally-exposed pixels from the captured images to generate optimally-exposed image data for each spectra, identifying a serum or plasma portion of the specimen, and classifying whether an interferent is present or absent within the serum or plasma portion. Testing apparatus and quality check modules adapted to carry out the method are described, as are other aspects.

24 Claims, 7 Drawing Sheets

(51) Int. Cl.
*G01N 21/31* (2006.01)
*G06T 7/00* (2017.01)

(52) U.S. Cl.
CPC ......... *G01N 21/314* (2013.01); *G01N 33/492* (2013.01); *G06T 7/0012* (2013.01); *G01N 2201/1293* (2013.01); *G06T 2207/10024* (2013.01); *G06T 2207/10048* (2013.01); *G06T 2207/20076* (2013.01); *G06T 2207/20081* (2013.01)

(58) Field of Classification Search
CPC .......... G01N 2201/1293; G06T 7/0012; G06T 2207/20076; G06T 2207/20081; G06T 2207/10024; G06T 2207/10048
See application file for complete search history.

(56) References Cited

U.S. PATENT DOCUMENTS

| | | | |
|---|---|---|---|
| 8,101,431 B2 | 1/2012 | McDevitt et al. | |
| 8,310,658 B2 | 11/2012 | Wardlaw et al. | |
| 9,322,761 B2 | 4/2016 | Miller | |
| 9,646,375 B2 * | 5/2017 | Satish | G06T 7/0012 |
| 10,267,813 B1 * | 4/2019 | Bhatia | G01N 35/00732 |
| 10,746,665 B2 | 8/2020 | Kluckner et al. | |
| 10,746,753 B2 | 8/2020 | Kluckner et al. | |
| 2005/0037505 A1 * | 2/2005 | Samsoondar | B01L 3/508 436/80 |
| 2005/0163354 A1 | 7/2005 | Ziegler | |
| 2010/0013983 A1 | 1/2010 | Ward et al. | |
| 2012/0140230 A1 | 6/2012 | Miller | |
| 2012/0309636 A1 | 12/2012 | Gibbons et al. | |
| 2013/0076882 A1 | 3/2013 | Itoh | |
| 2018/0365530 A1 | 12/2018 | Kluckner et al. | |
| 2018/0372648 A1 | 12/2018 | Wissmann et al. | |
| 2018/0372715 A1 | 12/2018 | Kluckner et al. | |
| 2019/0033209 A1 | 1/2019 | Kluckner et al. | |
| 2019/0041318 A1 | 2/2019 | Wissmann et al. | |

FOREIGN PATENT DOCUMENTS

| | | |
|---|---|---|
| WO | 03/031954 A1 | 4/2003 |
| WO | 2011/044660 A1 | 4/2011 |
| WO | 2016/133900 A1 | 8/2016 |

OTHER PUBLICATIONS

PCT International Search Report and Written Opinion dated Apr. 6, 2017 (9 Pages).

* cited by examiner

METHODS AND APPARATUS FOR DETECTING AN INTERFERENT IN A SPECIMEN

RELATED APPLICATION

This application claims priority to U.S. Provisional Patent Application Ser. No. 62/288,375 entitled "METHODS AND APPARATUS FOR DETECTING AN INTERFERENT IN A SPECIMEN" filed on Jan. 28, 2016, the disclosure of which is hereby incorporated by reference in its entirety herein.

FIELD

The present invention relates to methods and apparatus for testing of a specimen, and, more particularly to methods and apparatus for determining a presence of an interferent in a specimen, such as hemolysis, icterus, or lipemia (HIL).

BACKGROUND

Automated testing systems may be used to conduct clinical chemistry or assay testing using one or more reagents to identify an analyte or other constituent in a specimen such as urine, blood serum, blood plasma, interstitial liquid, cerebrospinal liquids, or the like. For convenience and safety reasons, these specimens may be contained in specimen containers (e.g., specimen collection tubes). The assay or test reactions generate various changes that may be read and/or manipulated to determine a concentration of analyte or other constituent present in the specimen.

Improvements in automated testing technology have been accompanied by corresponding advances in pre-analytical specimen preparation and handling operations such as sorting, batch preparation, centrifuging of specimen containers to separate specimen constituents, cap removal to facilitate specimen access, and the like by automated, pre-analytical, specimen preparation systems, which may be part of a Laboratory Automation System (LAS). The LAS may automatically transport specimens in specimen containers to a number of pre-analytical specimen processing stations as well as to analyzer stations containing clinical chemistry analyzers and/or assay instruments.

These LASs may handle processing of a number of different specimens at one time, which may be contained in barcode-labeled specimen containers. The barcode label may contain an accession number that may be correlated to demographic information that may be entered into a hospital's Laboratory Information System (LIS) along with test orders and/or other information. An operator may place the labeled specimen containers onto the LAS system, which may automatically route the specimen containers for pre-analytical operations such as centrifugation, decapping, and aliquot preparation, and all prior to the specimen actually being subjected to clinical analysis or assaying by one or more analyzers (clinical chemistry or assaying instruments) that may be part of the LAS.

For certain tests, such as for detection of an interferent, such as hemolysis, icterus, and lipemia (hereinafter collectively "HIL"), a serum or plasma portion obtained from whole blood by fractionation (e.g., by centrifugation) may be used. A gel separator may be added to the specimen container to aid in the separation of the settled blood portion from the serum or plasma portion in some cases. After fractionation and a subsequent de-capping process, in some embodiments the specimen container may be transported to an appropriate analyzer that may extract, via aspiration, serum or plasma portion from the specimen container and combine the serum or plasma portion with one or more reagents in a reaction vessel (e.g., cuvette or other vessel). Analytical measurements may then be performed, often using a beam of interrogating radiation, for example, or by using photometric or fluorometric absorption readings, or the like. The measurements allow determination of endpoint or rate values, from which a concentration of analyte or other constituent may be determined using well-known techniques.

Unfortunately, the presence of an interferent (e.g., H, I, and/or L) in the specimen, as a result of a patient condition or sample processing, may possibly adversely affect the test results of the analyte or constituent measurement obtained from the analyzer. For example, the presence of hemolysis in the specimen, which may be unrelated to the patient disease state, may cause a different interpretation of the disease condition of the patient. Moreover, the presence of icterus and/or lipemia in the specimen may also cause a different interpretation of the disease condition of the patient.

In the prior art, the integrity of the serum or plasma portion of the specimen may be visually inspected and rated for a degree (e.g., index) of HIL by a skilled laboratory technician. This may involve a review of the color of the serum or plasma portion of the specimen against known standards. A normal serum or plasma portion has a light yellow to light amber color. Serum or plasma portion containing hemolysis may have a reddish color. Serum or plasma portion containing icterus may have a dark yellow color due to increased bilirubin, and serum or plasma portion containing lipemia may have a whitish or milky appearance. However, such visual inspection is very subjective, labor intensive, and fraught with the possibility of human error.

Because manual inspection includes the problems listed above, it is becoming increasingly important to evaluate the integrity of the specimen without the use of visual inspection by a laboratory technician, by rather by using an automated inspection method. However, in some instances, barcode labels adhered directly to the specimen container may partially occlude the view of the specimen, so that there may not be clear opportunity to visually observe the serum or plasma portion. Thus, automation is difficult.

To accommodate for this, some systems, such as those described in U.S. Pat. No. 9,322,761 to Miller, describe automated pre-screening for HIL by rotating the specimen container to find a view window that is unobstructed by the label. However, such systems may be less prone to ease of automation.

Because of problems encountered when hemolysis, icterus, or lipemia (HIL) is contained within a specimen to be analyzed, there is an unmet need for a method and apparatus adapted to readily determine a presence of HIL and possibly the extent thereof. The method and apparatus should not appreciably adversely affect the speed at which analytical or assaying test results are obtained, i.e., the time to determine the presence of HIL should be very short. Furthermore, the method and apparatus should be able to be used even on labeled specimen containers where the label occludes some portion of the specimen.

SUMMARY

According to a first aspect, a method of determining an interferent in a specimen contained within a specimen container is provided. The method includes providing a specimen contained in a specimen container, capturing images of the specimen at multiple different exposure times and at multiple spectra having different nominal wavelengths, selection of optimally-exposed pixels from the captured images at the different exposure times at each spectra to generate optimally-exposed image data for each spectra, classifying a serum or plasma portion of the specimen, and determining whether an interferent is: present within the serum or plasma portion, or absent within the serum or plasma portion.

According to another aspect, a quality check module adapted to determine presence of an interferent in a specimen contained within a specimen container is provided. The quality check module includes a plurality of cameras arranged around the specimen container and configured to capture multiple images of the specimen at multiple different exposure times and multiple spectra having different nominal wavelengths and from multiple viewpoints, and a computer coupled to the plurality of cameras and adapted to process image data of the multiple images, the computer configured and capable of being operated to: select optimally-exposed pixels from the multiple images at the different exposure times for each spectra and generate optimally-exposed image data for each spectra, classify a serum or plasma portion of the specimen, and classify whether an interferent is: present within the serum or plasma portion, or absent within the serum or plasma portion.

In another aspect, a specimen testing apparatus adapted to determine presence of an interferent in a specimen contained within a specimen container is provided. The specimen testing apparatus includes a track, a carrier moveable on the track and configured to contain the specimen container, a plurality of cameras arranged around the track and configured to capture multiple images of the specimen at multiple different exposure times and multiple spectra having different nominal wavelengths and from multiple viewpoints, and a computer coupled to the plurality of cameras and configured to process image data from the multiple images, the computer configured and capable of being operated to: select optimally-exposed pixels from the multiple images at the different exposure times and spectra to generate optimally-exposed image data for each spectra, classify a serum or plasma portion of the specimen, and classify whether an interferent is: present within the serum or plasma portion, or absent within the serum or plasma portion.

Still other aspects, features, and advantages of the present invention may be readily apparent from the following description by illustrating a number of example embodiments and implementations, including the best mode contemplated for carrying out the present invention. The present invention may also be capable of other and different embodiments, and its several details may be modified in various respects, all without departing from the scope of the present invention. The invention is to cover all modifications, equivalents, and alternatives falling within the scope of the appended claims.

BRIEF DESCRIPTION OF THE DRAWINGS

The drawings, described below, are for illustrative purposes only and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Figure 1:
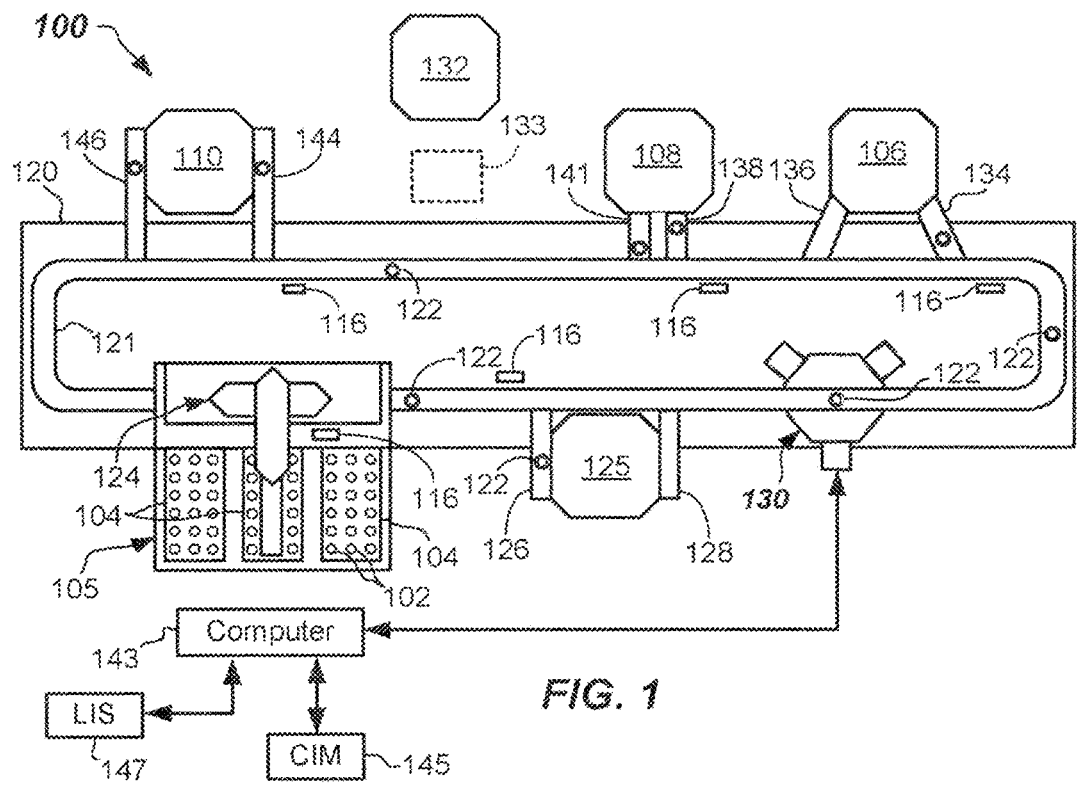
FIG. 1 illustrates a top view of a specimen testing apparatus including one or more quality check modules and one or more analyzers (clinical chemistry or assay instruments) according to one or more embodiments.

In a first broad aspect, embodiments of the present invention provide methods and apparatus configured to determine if one or more interferent are present in a serum or plasma portion of a specimen, or whether the serum or plasma portion is normal, i.e., does not contain an interferent. "Interferent," as used herein, shall mean the presence of at least one of hemolysis (H), icterus (I), or lipemia (L) in the serum or plasma portion of the specimen. Hemolysis (H), icterus (I), and lipemia (L) are collectively referred to as HIL herein.

"Hemolysis" as used herein is defined as a condition in the serum or plasma portion wherein red blood cells are destroyed, which leads to the release of hemoglobin from within the red blood cells into the serum or plasma portion such that the serum or plasma portion takes on a reddish hue.

"Icterus" as used herein means a condition of the blood where the serum or plasma portion is discolored dark yellow caused by an accumulation of bile pigment (bilirubin) in the blood.

"Lipemia" as used herein means a presence in the blood of an abnormally high concentration of emulsified fat, such that the serum or plasma portion includes a whitish or milky appearance.

The presence of one or more interferent (HIL) in the serum or plasma portion may affect the interpretation of results of the subsequent testing on an analyzer (e.g. clinical chemistry or assay testing). Thus, the ability to pre-screen for HIL before final analysis may minimize wasted time analyzing specimens that are not of the proper quality for analysis. Specimens that are found to contain or more of HIL may be flagged to the operator, scheduled for redraw, subjected to remediation, or subjected to further testing to more accurately measure an extent of the interferent that is present.

The specimen, as described herein, is generally collected in a specimen container, such as a blood collection tube and includes a settled blood portion and a serum and plasma portion after fractionation (e.g., separation by centrifugation). The settled blood portion is made up blood cells such as white blood cells (leukocytes), red blood cells (erythrocytes), and platelets (thrombocytes), which are aggregated and separated from the serum or plasma portion. The settled blood portion is generally found at a bottom part of the specimen container. The serum or plasma portion is the liquid component of blood, which is not part of the settled blood portion. It is generally found above the settled blood portion after fractionation. Plasma and serum differ in the content of coagulating components, primarily fibrinogen. Plasma is the unclotted liquid, whereas serum refers to blood plasma, which has been allowed to clot either under the influence of endogenous enzymes or exogenous components. In some specimen containers, a small gel separator may be used, which positions itself between the settled blood portion and the serum or plasma portion during centrifugation. The gel separator serves as a physical barrier between the two portions.

In accordance with one or more embodiments, the interferent detection method may be carried out as a pre-analytical testing method, i.e., taking place before carrying out analysis on an analyzer (e.g., clinical chemistry or assaying instrument). The HIL detection method described herein may use high dynamic range (HDR) image processing of the serum or plasma portion of the specimen to determine the presence of an interferent (H, I, and/or L). In some embodiments, the identification of the physical boundaries of the serum or plasma portion may also take place by using HDR image processing.

In some embodiments, a quality check module may be configured to carry out the interferent detection method. The quality check module may be provided in an area where a robotic mechanism (e.g., a track or gripper-finger robot) may transport specimens contained in specimen containers to the quality check module. In some embodiments, the quality check module may be provided on a track, where the track carries the specimens to remote locations for analysis (e.g., clinical chemistry testing or assaying) on an analyzer. In a specific embodiment, the quality check module may be provided on the track so that the specimen may be tested for the presence of an interferent while resident on the track.

In one or more embodiments, the processed HDR data may be used for HIL detection. In a further embodiment, the HDR data may also be used for artifact detection (e.g., the detection of clot, bubble, or foam in the serum or plasma portion). In this case, the pixels that are found to contain an artifact may simply be ignored in carrying out the determination of HIL based upon the processed HDR data, as the artifact location(s) and extent is now known. Should the specimen be found to contain one or more of H, I, and L, the specimen may then be taken off line to perform a remediation to rectify the one or more of H, I, or L, further quantification of the extent of the HIL, for a redraw, or other processing. The interferent detection method is image based, i.e., based on pixelated images obtained by multiple digital cameras at multiple viewpoints. "Pixel" as used herein means either a single pixel or a grouping of pixels, such as a super-pixel. A super pixel having a size of 11 individual pixels by 11 individual pixels was found to work well for processing the data.

In another related aspect of the invention, the data obtained from the HIL analysis can be used to determine the volume of the serum or plasma portion, and also possibly a volume of the settled blood portion. The data may also be used to determine a liquid-air interface (LA), an interface between serum or plasma portion and the settled blood portion (SB), an interface between serum or plasma portions and gel separator (SG), and/or an interface between settled blood portion and gel separator (BG).

The HIL detection method including HDR data processing may include capturing multiple images at the quality check module at multiple exposure times and at multiple spectra having different nominal wavelengths and also from the multiple viewpoints using a plurality of cameras. "Camera" as used herein means any device capable of capturing a pixelated image (e.g., digital image) for analysis. The exposure time may vary based on the lighting intensity and camera features, but multiple exposure times may be used for each spectrum and for each camera. For each camera, the exposure time may be the same for each corresponding image capture.

For each corresponding pixel of the multiple images at a particular wavelength, pixels exhibiting optimal image intensity may be selected. The result is a plurality of consolidated color image data sets for each different spectra (e.g., red, green, blue, near infrared, infrared) where all of the pixels are optimally exposed (e.g., one image data set per spectra. The data from the consolidated color data sets may be subject to statistical analysis to determine statistical data on each pixel (e.g., mean, standard deviation, and covariance matrix) thereof. Covariance is a measure of how much two or more of the color pixels change together. This statistical data, in the form of one or more data matrices, can then be operated on by or more multi-class classifiers in order to segment the image data set into classes.

In some embodiments, the HDR data may be passed through the multi-class classifier to additionally determine the area of the serum or plasma portion in the image, as well as other classes (e.g., settled blood portion, gel separator, tube, cap, label, air). The multi-class classifier may be a support vector machine (SVM) or a random decision tree that has been pre-trained from multiple training sets. Once the serum or plasma portion is identified by the multi-class classifier, one or more interferent classifiers may be used to identify the presence of an interferent (e.g., H, I, and/or L). The one or more interferent classifiers may be individually-trained binary models that may classify each pixel as being H, I, or L respectively. In other embodiments, the interferent classifier may be a multi-class classifier. The interferent classifier models may each also be a support vector machine (SVM) or a random decision tree.

Based upon the interferent classification results, an interferent type for the serum or plasma portion, as a whole, may be determined (i.e., H, I, and/or L). An interferent level for the determined interferent type(s) may also be optionally provided. The interferent level may be based upon one or more additional models (e.g., one or more regression models) in some embodiments. The regression models may be trained for each interferent type based upon sample specimens that exhibit diverse interference levels. More than one interferent type may be determined by the method, and an interferent level for each determined interferent type may be specified thereby.

Further details of inventive interferent detection methods, quality check modules, and specimen testing apparatus including a quality check module will be further described with reference to FIGS. 1-7 herein.

Figure 2:
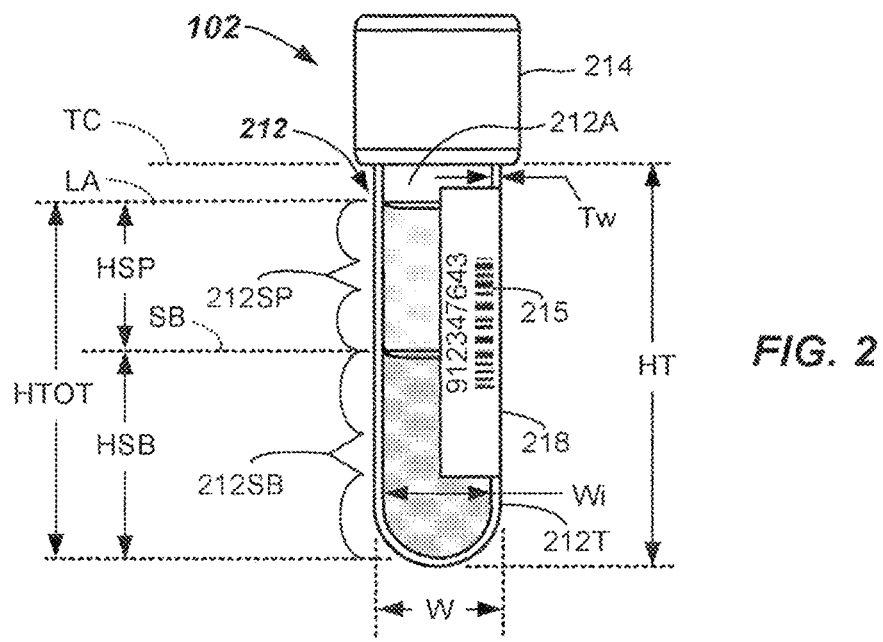
FIG. 2 illustrates a side view of a labeled specimen container including a separated specimen containing an interferent, which may be determined by using an interferent detection method according to one or more embodiments.
Figure 3:
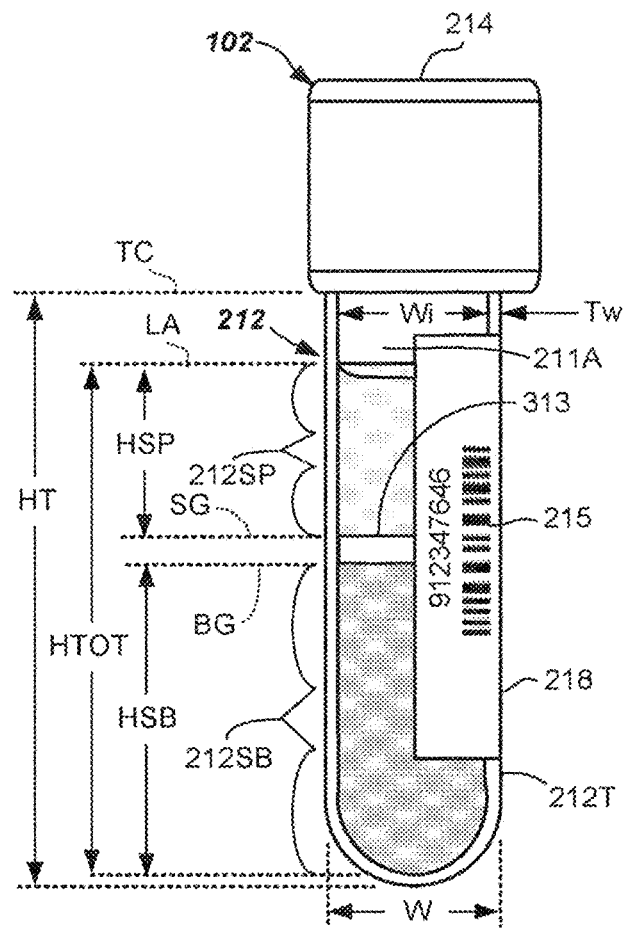
FIG. 3 illustrates a side view of a labeled specimen container including a separated specimen containing an interferent and a gel separator, wherein a presence of the interferent may be determined by using an interferent detection method according to one or more embodiments.

FIG. 1 shows a specimen testing apparatus 100 capable of automatically processing multiple specimen containers 102 (e.g., specimen collection tubes—see FIGS. 2 and 3). The specimen containers 102 may be contained in one or more racks 104 at a loading area 105 prior to transportation to, and analysis by, one or more analyzers (e.g., first, second, and third analyzer 106, 108, 110, respectively, arranged about the specimen testing apparatus 100). It should be apparent that more or less numbers of analyzers can be used. The analyzers may be any combination of clinical chemistry analyzers and/or assaying instruments, or the like. The specimen containers 102 may be any generally transparent or translucent container, such as a blood collection tube, test tube, sample cup, cuvette, or other generally clear glass or plastic container.

Typically, specimens 212 (FIGS. 2 and 3) to be automatically processed may be provided to the specimen testing apparatus 100 in the specimen containers 102, which may be capped with a cap 214 (FIGS. 2 and 3—otherwise referred to as a stopper). The caps 214 may have different shapes and/or colors (e.g., red, royal blue, light blue, green, grey, tan, yellow, or color combinations) which may have meaning in terms of the test the specimen container 102 is used for, the type of additive, or the like. Other cap colors may be used.

Each of the specimen containers 102 may be provided with identification information 215 (i.e., indicia), such as a barcode, alphabetic, numeric, alphanumeric, or combination thereof that may be machine readable at various locations about the specimen testing apparatus 100. The identification information 215 may indicate, or may otherwise be correlated to, via a Laboratory Information System (LIS), a patient's identification as well as tests to be accomplished upon the specimen 212, or other information, for example. Such identification information 215 may be generally provided on a label 218 adhered to, or otherwise provided on the side of, the specimen container 102. The label 218 generally does not extend all the way around the specimen container 102, or all along a length of the specimen container 102. In some embodiments multiple labels may be adhered, and may slightly overlap. Accordingly, although the label 218 may occlude some portion of the specimen 212, but some portion of the specimen 212 may still be viewable. In some embodiments, the racks 104 may have additional identification information thereon.

The specimen 212 may include a serum or plasma portion 212SP and a settled blood portion 212SB contained within the tube 212T. Air 212A may be provided above the serum and plasma portion 212SP and the line or demarcation between them is defined herein as the liquid-air interface (LA). The line of demarcation between the serum or plasma portion 212SP and the settled blood portion 212SB is defined herein as the serum-blood interface (SB) and is shown in FIG. 2. The interface between the air 212A and the cap 214 is referred to herein as the tube-cap interface (TC). The height of the tube (HT) is defined as the height from the bottom-most part of the tube 212T to the bottom of the cap 214. The height of the serum or plasma portion 212SP is (HSP) and is defined as the height from the top of the serum or plasma portion 212SP from the top of the settled blood portion 212SB, i.e., from LA to SB in FIG. 2. The height of the settled blood portion 212SB is (HSB) and is defined as the height from the bottom of the settled blood portion 212SB to the top of the settled blood portion 212SB at SB in FIG. 2. HTOT is the total height of the specimen 212 and equals HSP plus HSB in FIG. 2.

In cases where a gel separator 313 is used (FIG. 3), the height of the serum or plasma portion 212SP is (HSP) and is defined as the height from the top of the serum or plasma portion 212SP at LA to the top of the gel separator 313 at SG, i.e., from LA to SG in FIG. 3. The height of the settled blood portion 212SB is (HSB) and is defined as the height from the bottom of the settled blood portion 212SB to the bottom of the gel separator 313 at BG in FIG. 3. HTOT is the total height of the specimen 212 and equals HSP plus HSB plus a height of the gel separator 313. In each case, the wall thickness is Tw, the outer width is W, and the inner width of the specimen container 102 is Wi.

In more detail, specimen testing apparatus 100 may include a base 120 (e.g., a frame or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to locations spaced about the track 121 in carriers 122.

Carriers 122 may be passive devices, i.e., non-motored pucks that may be configured to carry a single specimen container 102 on the track 121 or an automated carrier including an onboard drive motor, such as a linear motor, that is programmed or otherwise controlled to move about the track 121 and stop at pre-programmed locations. Carriers 122 may each include a holder 122H (FIGS. 4A-4D) configured to hold the specimen container 102 in a defined upright position. The holder 122H may include a plurality of fingers or leaves that secure the specimen container 102 in the carrier 122, but may be moveable or flexible to allow for different sizes of specimen containers 102 to be received therein. In some embodiments, carriers 122 may leave from the loading area 105 having one or more racks 104 staged thereat. In some embodiments, loading area 105 may serve a dual function of allowing offloading of the specimen containers 102 from the carriers 122 after analysis is completed.

A robot 124 may be provided at the loading area 105 and may be configured to grasp the specimen containers 102 from the one or more racks 104 and load the specimen containers 102 onto the carriers 122, such as on an input lane of the track 121. Robot 124 may also be configured to remove specimen containers 102 from the carriers 122 upon completion of testing. The robot 124 including one or more (e.g., least two) robot arms or components capable of X and Z, Y and Z, X, Y, and Z, or r and theta motion. Robot 124 may be a gantry robot, an articulated robot, an R-theta robot, or other suitable robot wherein the robot 124 may be equipped with robotic gripper fingers sized to pick up and place the specimen containers 102. Upon being loaded onto track 121, the specimen containers 102 carried by carriers 122 may progress to a centrifuge 125 (e.g., an automated centrifuge configured to carry out fractionation of the specimen 212). Carriers 122 carrying specimen containers 102 may be diverted to the centrifuge 125 by inflow lane 126 or other suitable robot. After being centrifuged, the specimen containers 102 may exit on outflow lane 128, or otherwise be removed by a robot, and continue on the track 121. In the depicted embodiment, the specimen container 102 in carrier 122 may next be transported to a quality check module 130 to be further described herein with reference to FIGS. 4A and 4D.

The quality check module 130 is configured and adapted for automatically determining a presence of one or more of H, I, and/or L contained in a specimen 212 to be processed by the specimen testing apparatus 100. If found to contain effectively low amounts of H, I and/or L so as to be considered normal (N), the specimen 212 may continue on the track 121 and then may be analyzed in the one or more analyzers (e.g., first, second and third analyzers 106, 108, and/or 110) before returning each specimen container 102 to the loading area 105 for offloading. In some embodiments, the specimen 212 may also be tested for the presence of an artifact (e.g., clot, bubble, or foam) at the quality check module 130. In some embodiments, quantification of the specimen 212 may take place at the quality check module 130 (i.e., determination of HSP, HSB, HTOT, and determination of location of SB, LA). In some embodiments, quantification of the physical attributes of the specimen container 102 may take place at the quality check module 130 such as determining HT, cap color, cap type, TC, and tube width (W).

Additionally, a remote station 132 may be provided on the automated specimen testing apparatus 100 even though the remote station 132 is not directly linked to the track 121. For instance, an independent robot 133 (shown dotted) may carry specimen containers 102 containing specimens 212 to the remote station 132 and return them after testing/processing. Optionally, the specimen containers 102 may be manually removed and returned. Remote station 132 may be used to test for certain constituents, such as a hemolysis level, or may be used for further processing, such as to lower a lipemia level through one or more additions, or to remove a clot, bubble or foam, for example. Other testing or processing may be accomplished at remote station 132. Other stations (not shown) may be provided or arranged along the track 121, such as a de-capping station, or the like.

The specimen testing apparatus 100 may include a number of sensors 116 at one or more locations around the track 121. Sensors 116 may be used to detect a location of specimen containers 102 along the track 121 by means of reading the identification information 215 (FIG. 2) placed on the specimen container 102, or like information (not shown) that is provided on each carrier 122. In some embodiments, a distinct RFID chip may be embedded in each carrier 122 and conventional RFID reader system may be employed in the tracking operation, for example. Other means for tracking the location of specimen containers 102 in the carriers 122 may be used, such as proximity sensors. All of the sensors 116 may interface with the computer 143 so that the location of each specimen container 102 may be appropriately known at all times.

Centrifuge 125 and each of the analyzers 106, 108, 110 may be generally equipped with robotic mechanisms and/or inflow lanes (e.g., inflow lanes 126, 134, 138, 144) configured to remove carriers 122 from the track 121, and robotic mechanisms and/or outflow lanes (e.g., outflow lanes 128, 136, 141, and 146) configured to reenter carriers 122 to the track 121.

Specimen testing apparatus 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the specimen testing apparatus 100. The computer 143 may operate to control movement of the carriers 122 to and from the loading area 105, motion about the track 121, motion to and from the centrifuge 125 as well as operation of the centrifuge 125, motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry).

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y., and such control is typical to those skilled in the art of computer-based electromechanical control programming and will not be further described herein. However, other suitable systems for controlling the specimen testing apparatus 100 may be used. The control of the quality check module 130 may also be provided by the computer 143, but according to an inventive model-based method, as will be described in detail herein.

Embodiments of the present invention may be implemented using a computer interface module (CIM) that allows for a user to easily and quickly access a variety of control screens and status display screens. These control and status screens may describe some or all aspects of a plurality of interrelated automated devices used for preparation and analysis of specimens 212. The CIM may employed to provide information about the operational status of a plurality of interrelated automated devices as well as information describing the location of any specimen 212 as well as a status of tests to be performed on, or being performed on, the specimen 212. The CIM 145 is thus adapted to facilitate interactions between an operator and the specimen testing apparatus 100. The CIM 145 may include a display screen adapted to display a menu including icons, scroll bars, boxes, and buttons through which the operator may interface with the specimen testing apparatus 100. The menu may comprise a number of function buttons programmed to display functional aspects of the specimen testing apparatus 100.

In FIGS. 2 and 3, specimen containers 102 including one of H, I or L are shown. FIG. 2 illustrates a specimen 212 including H, I, or L in the serum or plasma portion 212SP without a gel separator. FIG. 3 illustrates a specimen 212 including H, I, or L in the serum or plasma portion 212SP with a gel separator 313. Pre-screening the specimen containers 102 for the presence of an interferent ensures that the specimen 212 can be stopped from progressing on to the one or more analyzers 106, 108, 110, if desired. In this way, inaccurate test results may be avoided. In some embodiments, if the method determines that an interferent exists, then the specimen container 102 may be taken offline, such as to remote station 132 for remedial action (e.g., lipemia reduction), for better quantification of the level of hemolysis or icterus, which can be reported along with the test results, or possibly to have the specimen 212 redrawn.

Figure 4A:
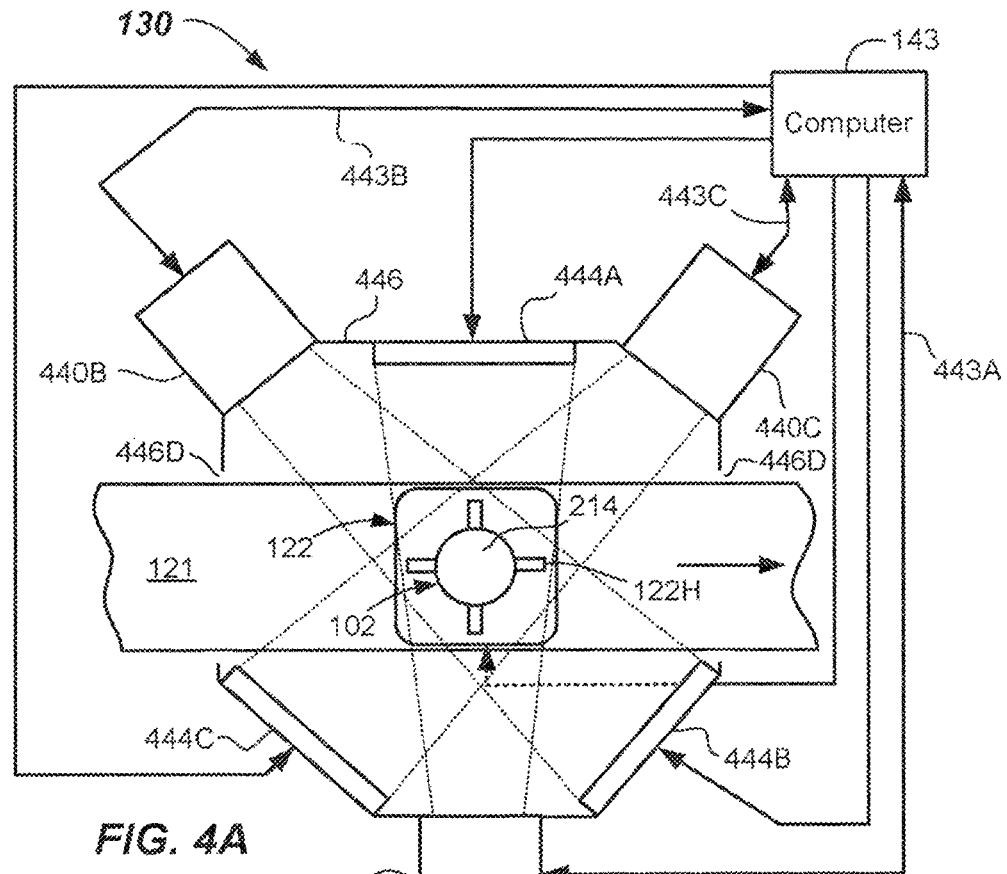
FIG. 4A illustrates a schematic top view (with ceiling removed) of a quality check module configured to capture and analyze multiple images for a presence of an interferent in a specimen according to one or more embodiments.
Figure 4B:
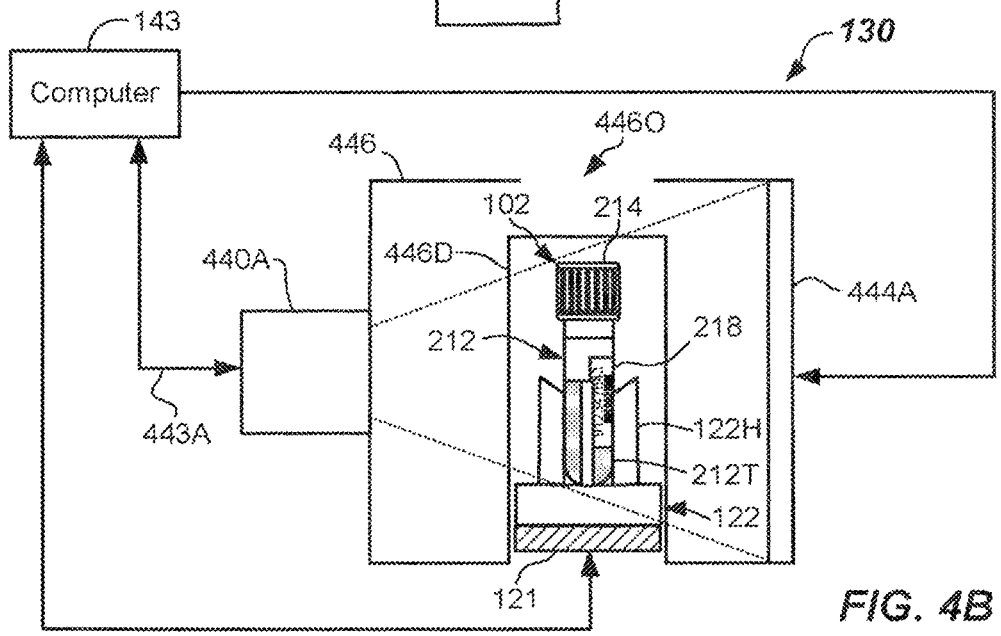
FIG. 4B illustrates a schematic side view (with side removed) of the quality check module of FIG. 4A according to one or more embodiments.

With reference to FIGS. 4A-4B, a first embodiment of a quality check module 130 is shown and described. Quality check module 130 may be configured and adapted to automatically determine a presence of an interferent (e.g., H, I, or L) in a specimen 212 (e.g., in a serum or plasma portion 212SP thereof) prior to analysis by the one or more analyzers 106, 108, 110. Pre-screening in this manner allows for additional processing, additional quantification, discarding, or redraw of a specimen 212 without wasting valuable analyzer resources or possibly having the presence of an interferent affect the veracity of the test results.

In addition to the interferent detection method, other detection methods may take place on the specimen 212 contained in the specimen container 102 at the quality check module 130. Further, a detection method may be used to quantify one or more geometrical features of the specimen container 102. For example, the quality check module 130 may be used to quantify the specimen 212, i.e., determine certain physical dimensional characteristics of the specimen 212 (e.g., a physical location of LA and SB, and/or determination of HSP, HSB, and/or HTOT, and/or a volume of the serum or plasma portion (VSP) and/or a volume of the settled blood portion (VSB)). Further, in some embodiments, an artifact detection method may determine the presence or absence of an artifact (e.g., clot, bubble, or foam) in the serum or plasma portion 212SP.

In one or more embodiments, the quality check module 130 may be used to quantify the specimen container 102, i.e., quantify one or more physical dimensional characteristics of the specimen container 102, such as the location of TC, HT, and/or W of the specimen container 102, and/or a color of and/or type of the cap 214.

Now referring to FIGS. 1, 4A, and 4B, a first embodiment of a quality check module 130 is provided that may include multiple cameras 440A-440C. Three cameras 440A-440C are shown, but two or more, three or more, four or more can be used. Cameras 440A-440C may be conventional digital cameras capable of capturing a digital image (i.e., a pixelated image), charged coupled devices (CCD), an array of photodetectors, one or more CMOS sensors, or the like. For example, three cameras 440A, 440B, 440C are illustrated in FIG. 4A and are configured to capture images from three different viewpoints (e.g., lateral viewpoints). Each camera 440A, 440B, 440C may be a device capable of capturing an image having an image size. In one embodiment, the image size may be about 2560×694 pixels, for example. In another embodiment, the image size may be about 1280×384 pixels, for example. Other pixel densities may be used. Each camera 440A, 440B, 440C may be configured and operable to capture lateral images of at least a portion of the specimen container 102, and at least a portion of the specimen 212. For example, the cameras 440A-440C may capture a part of the label 218 or cap 214 and part of the tube 212T, and at least a portion of the serum or plasma portion 212SP. Eventually, from the multiple images, a composite model of the specimen 212 in the specimen container 102 can be developed. The composite model may be a 3D model including classification results in some embodiments, and may be used to make final determinations about the specimen 212.

In the embodiment shown, the plurality of cameras 440A, 440B, 440C are arranged around the specimen 212 and configured to capture lateral images from multiple viewpoints. The viewpoints may be spaced so that they are approximately equally spaced from one another, such as about 120 degrees from one another, as shown, when three cameras 440A, 440B, 440C are used. As depicted, the cameras 440A, 440B, 440C may be arranged around the track 121. Other arrangements of the plurality of cameras 440A, 440B, 440C may be used. In some embodiments, the images of the specimen 212 in the specimen container 102 may be taken while the specimen container 102 is residing in the carrier 122. The images may overlap slightly.

In one or more embodiments, the carriers 122 may be stopped at a pre-determined location in the quality check module 130, such as at a point where normal vectors from each of the cameras 440A, 440B, 440C intersect. In some embodiments, a gate may be provided to stop the carriers 122, so that one or more good quality images may be captured thereat. In other embodiments, the carriers 122 may include a linear motor configured to start and stop the carrier 122 at desired locations, as programmed. In an embodiment where there is a gate at the quality check module 130, one or more sensors (like sensors 116) may be used to determine the presence of a carrier 122 at the quality check module 130.

The cameras 440A, 440B, 440C may be provided in close proximity to and trained or focused to capture an image window, i.e., an area including an expected location of the specimen container 102, wherein the specimen container 102 may be stopped so that it is approximately located in a center of the view window. As configured, the cameras 440A, 440B, 440C can capture images that include portions of the serum or plasma portion 212SP, portions of the settled blood portion 212SB, and some or all of the tube 212T and some or all of the cap 214. Within the images captured, one or more reference datum may be present. The reference datum may aid in quantification of the specimen 212. Reference datum may be TC or the bottom-most portion of the specimen container 102, or a mark in a known location somewhere on the specimen container 102, for example a ring at a predetermined height, that can be viewed from all viewpoints.

In operation, each image may be triggered and captured responsive to a triggering signal provided in communication lines 443A, 443B, 443C that may be sent by the computer 143. Each of the captured images may be processed according to one or more embodiments of the method provided herein. In particular, HDR processing may be used to capture and process the images.

In more detail, multiple images are captured of the specimen 212 (e.g., the specimen separated by fractionation) at the quality check module 130 at multiple different exposures times and at one or more different wavelength spectra. For example, each camera 440A, 440B, 440C may take 4-8 images at different exposure times at one or more spectra (one or more wavelength ranges).

Figure 4C:
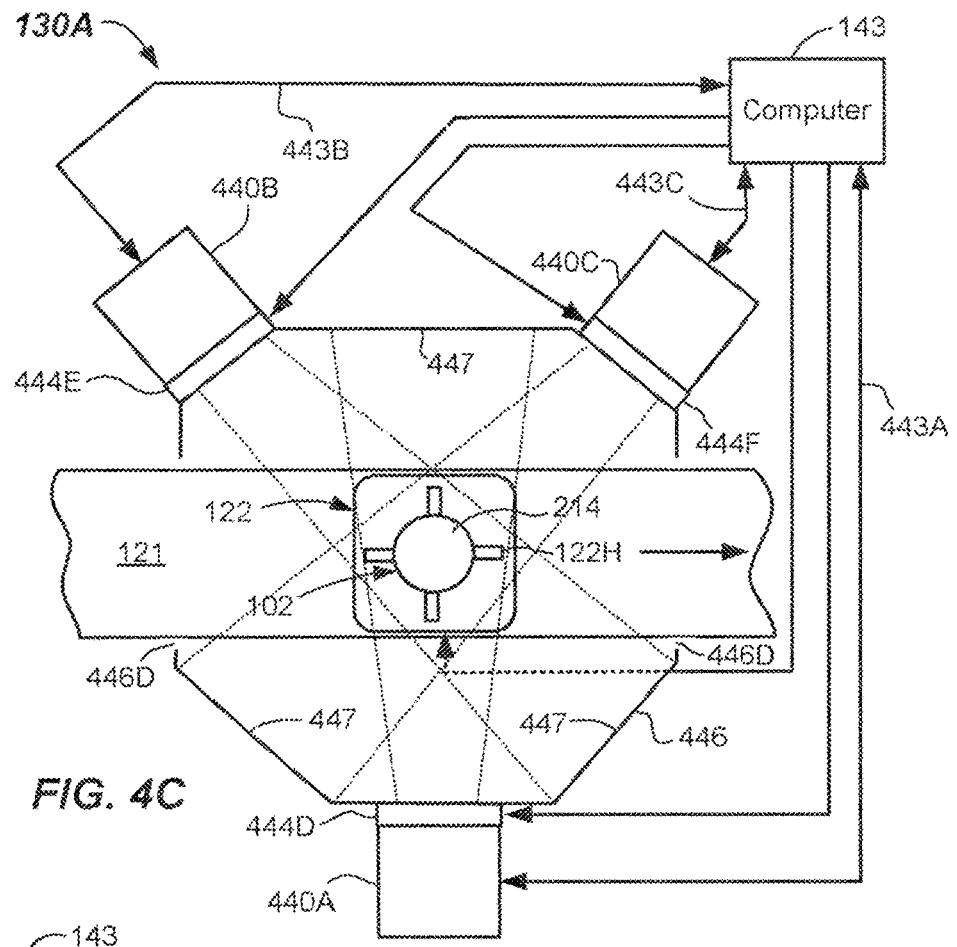
FIG. 4C illustrates a schematic top view (with ceiling removed) of a quality check module configured to capture and analyze multiple images for a presence of an interferent according to one or more embodiments.
Figure 4D:
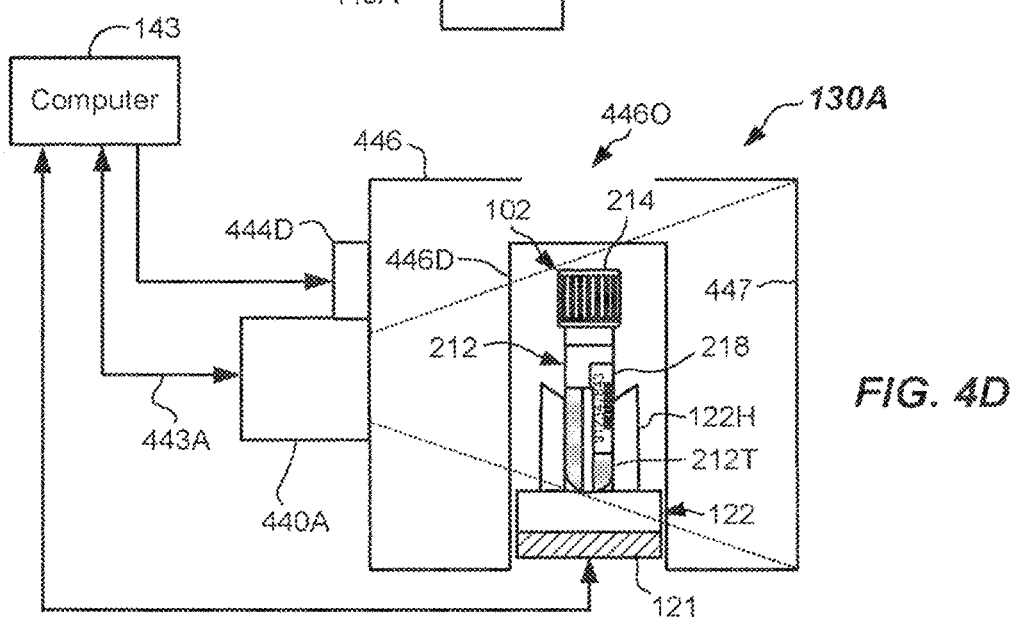
FIG. 4D illustrates a schematic side view (with side removed) of the quality check module of FIG. 4C according to one or more embodiments.

In one embodiment, the multiple wavelength images may be accomplished using different colored light sources 444A-444C emitting different spectral illumination. The light sources 444A-444C may back light the specimen container 102 (as shown). Optionally, light sources 444D-444F may front light the specimen container 102, such as by being arranged above, below, or to the side of the respective cameras 440A, 440B, 440C, or be elsewhere located and illuminated as shown in FIGS. 4C-4D. A light diffuser may be used in conjunction with the light sources 444A-444C or 444D-444F in some embodiments. The multiple different spectra light sources 444A-444C may be RGB or other light sources, such as LEDs emitting two or more different spectra. For example, the light sources may emit illumination to nominal wavelengths of 634 nm+/−35 nm (Red—R), 537 nm+/−35 nm (Green—G), and 455 nm+/−35 nm (Blue—B). In other embodiments, the illumination spectra may comprise one or more spectra having a nominal wavelength between about 700 nm and about 1500 nm, or even between about 700 nm and about 1200 nm.

For example, to capture images at a first wavelength, three red light sources (wavelength of about 634 nm+/−35 nm) may be used to illuminate the specimen 212 from three lateral locations. The red illumination by the light sources 444A-444C may occur as the multiple images (e.g., 4-8 images or more) at different exposure times are captured by each camera 440A-440C. In some embodiments, the exposure times may be between about 0.1 ms and 256 ms. Other exposure times may be used. Each of the respective images for each camera 440A-440O may be taken either sequentially or simultaneously.

In each embodiment, the quality check module 130, 130A may include a housing 446 that may at least partially surround or cover the track 121, and the specimen container 102 may be located inside the housing 446 during the image taking phase. Housing 446 may include one or more doors 446D (e.g., openings) to allow the carriers 122 to enter into and/or exit from the housing 446. In some embodiments, the ceiling may include an opening 446O to allow a specimen container 102 to be loaded into the carrier 122 by a robot including moveable robot fingers from above. In the case where front lighting (FIG. 4C-4D) is used, the quality check module 130A may include backstop walls 447 to provide improved image contrast. Backstop walls 447 may be any suitable color other than the expected range of color of the specimen 212. In some embodiments, a black colored material may be used.

Once the red illuminated images are captured in the embodiment of FIGS. 4A-4B, the red light sources 444A-444C may be turned off and one or more other spectra of light, for example, green light sources 444A-444C may be turned on (nominal wavelength of about 537 nm with a bandwidth of about +/−35 nm), and multiple images (e.g., 4-8 or more images) at different exposure times may be captured at that spectra by each camera 440A, 440B, 440C. This may be repeated with blue light sources 444A-444C (nominal wavelength of about 455 nm with a bandwidth of about +/−35 nm) for each camera 440A, 440B, 440C. In other embodiments, white light sources (400 nm-700 nm), near infrared (NIR) light sources (e.g., 700 nm to 1200 nm), or even infrared (IR) light sources (e.g., 1200 nm-1500 nm) may be used. The infrared (IR) and near infrared light (NIR) sources may be particularly effective at increasing the transmittance of both specimens 212 and labels 218, and allowing improved see-through capability. The NIR and IR light sources may also be beneficial for detecting liquid level (level of serum or plasma portion 212SP), despite occlusion by label 218. Further, discrimination of icteric versus lipemic specimens may be improved by using IR or NIR sources for lighting during imaging. The different nominal wavelength light sources 444A-444C may be accomplished via use of switchable bandpass filters, for example, or banks of different colored/spectral light sources that can be selectively turned on and off, for example. Other means for different spectral lighting may be used. Illumination and image capture at two or more, or even three or more, different spectra may be undertaken.

In the optional embodiment, as best shown in FIGS. 4C and 4D, the specimen container 102 may be front lit in the quality check module 130A, such as by including light sources 444D, 444E, and 444F arranged adjacent to the cameras 440A, 440B, 440C, i.e., above, below, to the side, or combinations, but on the same side of the specimen container 102 as the respective cameras 440A-440O. In this embodiment, the cameras 440A-440O may be digital color cameras having RGB nominal wavelength peaks at approximately 634 nm, 537 nm, and 455 nm, respectively, but wherein each of the RGB color spectra has a relatively wider wavelength range as compared to the discreet sources used in the above embodiment with the monochrome cameras. In this embodiment, the light sources 444D, 444E, and 444F may each be white light sources. For example, the light sources 444D-444F may emit a wavelength range as specified above and may be used to illuminate the specimen 212 from multiple lateral locations. Multiple images at different exposure times may be taken by each camera 440A-440O. Each white-light image taken may be separated into color components at multiple wavelengths. For example, computer 143 may separate the images into at least three captured wavelengths between about 400 nm and about 700 nm. For example, RGB components may be separated out of the images by the computer 143 to generate the multi-spectral, multi-exposure time captured images. Images may be taken as before via signals from the computer 143 in lines 443A-443C.

For each of the above setups, all of these multiple images taken at multiple exposure times for each respective wavelength spectra (e.g., R, G, and B) may be obtained in rapid succession, such that the entire collection of images for the specimen 212 from multiple viewpoints may be obtained in a short amount of time, such as less than about 2 seconds, for example. In one example, 4 different exposure images for each wavelength at three viewpoints using the cameras 440A, 440B, 440C and back lighting with RGB light sources 444A-444C will result in 4 images×3 colors×3 cameras=36 images. In another example, 4 different exposure images at three viewpoints using the cameras 440A, 440B, 440C and front lighting with white light sources 444D-444F will result in 4 images×3 cameras=12 images. However, RGB images are then captured by separating the white light images taken into the individual RGB components thereof. Thus, after separation, 36 images are also captured. The image data may be stored in memory of the computer 143 and subsequently processed thereby. Reference images may be taken in addition to these and used for background removal.

According to the HIL characterization method, the processing of the image data may involve, for example, selection of optimally-exposed pixels from the multiple captured images at the different exposure times at each wavelength spectra and for each camera 440A-440C so as to generate optimally-exposed image data for each wavelength spectra and for each camera 440A-440O. This is referred to as "image consolidation" herein. For each corresponding pixel, for each of the images from each camera 440A-440C, pixels exhibiting optimal image intensity may be selected from each of the different exposure time images. In one embodiment, optimal image intensity may be between 16-254 on a scale of 0-255, for example. In another example, optimal image intensity may be pixels that fall within a predetermined range of 180-254 on a scale of 0-255, for example. If more than one pixel in the corresponding locations of two images is determined to be optimally exposed, the higher of the two is selected. The selected pixels exhibiting optimal image intensity may be normalized by their respective exposure times. The result is a plurality of normalized and consolidated color image data sets (e.g., R, G, B) for each camera 440A-440O where all of the pixels are optimally exposed (e.g., one image data set per wavelength (e.g., R, G, and B). Image sets at near infrared and/or infrared may also or optionally be captured and processed to provide optimally exposed image data sets per viewpoint.

As part of the calibration process of the quality check module 130, reference images without a specimen container 102 or carrier 122 may be taken. In this way, computational burden may be minimized by subtracting tube background (the region outside of the specimen container 102) from each image data set. Reference images for each exposure time and lighting condition (R, G, B, white light, near IR, IR) may be taken by the quality check module 130 before carrying out the interferent detection method.

For each image data set including optimally-exposed pixels, a characterization process is undertaken to identify the pixels that are classified as serum or plasma portion 212SP of the specimen 212. Identifying the serum or plasma portion 212SP may be based on classifying each the pixels in the optimally-exposed image data. Classification may be based upon using a multi-class classifier generated from multiple training sets. The multi-class classifier may comprise a support vector machine (SVM) or a random decision tree, for example. Other means for determining the classification of the serum or plasma portion 212SP may be used.

To carry out the classification, first statistical data as described above may be computed for each of the optimally-exposed pixels at the different wavelength spectra (e.g., R, G, B, white light, near IR, and/or IR) for each camera 440A-440C. The statistical data may include mean values and covariance up to $2^{nd}$ order, for example. The calculated statistical attributes encode specific properties of object classes and are thus used for discrimination between the different object classes by assigning class labels. Once generated, the statistical data is presented to, and operated on, by a multi-class classifier 515, which may classify the pixels in the images as belonging to one of a plurality of class labels, such as 1—serum or plasma portion, 2—settled blood portion, 3—tube, 4—cap, 5—label, 6—air, and 7—gel separator (if used). From this, the pixels making up the liquid region (i.e., the serum and plasma portion 212SP) may be identified.

The multi-class classifier 515 may be any suitable type of supervised classification model that is linear or non-linear. For example, the multi-class classifier 515 may be a support vector machine (SVM) that is either linear or kernel-based. Optionally, the multi-class classifier 515 may be a boosting classifier such as an adaptive boosting classifier (e.g., Ada-Boost, LogitBoost, or the like), any artificial neural network, a tree-based classifier (e.g., decision tree, random decision forests), and logistic regression as a classifier, or the like. A SVM may be particularly effective for classification between liquids and non-liquids, such as found in the analysis of the specimen 212. A SVM is a supervised learning model with associated learning algorithms that analyzes data and recognizes patterns. SVMs are used for classification and regression analysis.

Multiple sets of training examples are used to train the multi-class classifier 515, and then the image data set is operated on multi-class classifier 515 and each pixel is classified. The multi-class classifier 515 may be trained by graphically outlining various regions in a multitude of examples of specimen containers 102 having various specimen conditions, occlusion by label 218, levels of serum or plasma portion 212SP and settled blood portions 212SB, and the like. As many as 500 or more images may be used for training the multi-class classifier 515. Each training image may be outlined manually to identify and teach the multi-class classifier 515 the areas that belong to each class.

A training algorithm builds the multi-class classifier 515 that assigns pixels of any new specimens into one of the classes. The SVM model represents examples as points in space that are mapped so that the examples of the separate classes are divided by a clear gap that is as wide as possible. New pixels from the image data set may be mapped into that same space and predicted to belong to a particular class based on which side of the gap they fall on. In some embodiments, SVMs can efficiently perform a non-linear classification using what is called a kernel trick (e.g., kernel-based SVM classifier), implicitly mapping their inputs into high-dimensional feature spaces. SVM and boosting are particularly preferred. Other types of classification models may be used.

The results of the multi-class classifier 515 that are deemed to be of the class of serum or plasma portion 212SP may then fed into a model configured to identify whether H, I, or L is present within the serum or plasma portion 212SP or whether no HIL is present and the specimen 212 is thus normal (N). Thus, effectively, the interferent model classifies, based on the image data subset, whether an interferent is present within one or more regions of the serum or plasma portion 212SP, or is absent within the serum or plasma portion 212SP. In one or more embodiments, the interferent model may be embodied as one or more different interferent type models, such as a hemolysis model, an icterus model, and a lipemia model. In some cases, even a normal model may be used. Each interferent or normal model may be a binary classification model. The result of operating on the image data subset previously defined as liquid is the presence of an interferent or the absence of an interferent in the serum or plasma portion 212SP, i.e., the serum or plasma portion 212SP of the specimen 212 is normal.

Figure 5:
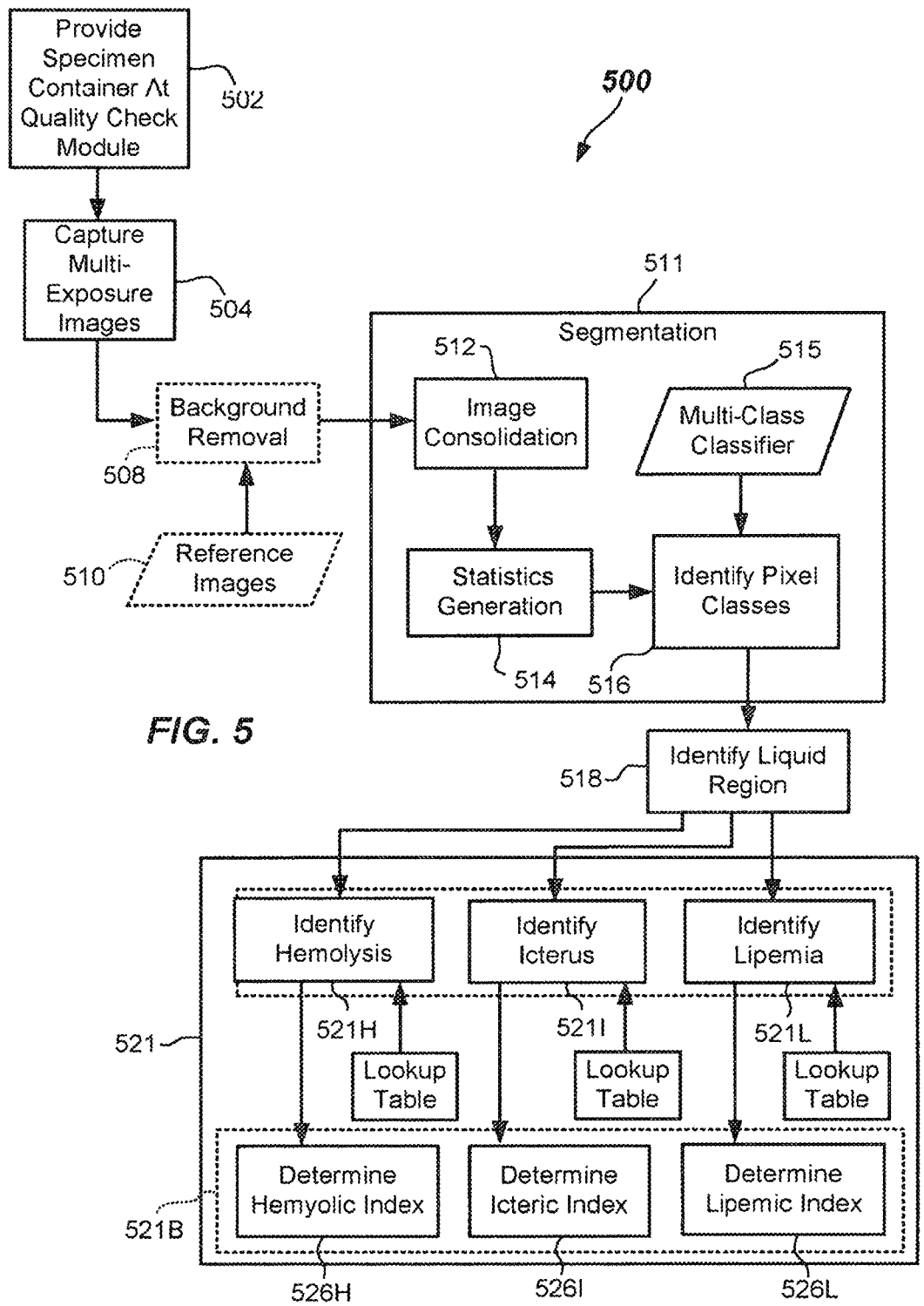
FIG. 5 illustrates a block diagram of components of a quality check module configured to determine a presence of an interferent in a specimen according to one or more embodiments.

A simple functional flow chart of the interferent detection method according to one or more embodiments is shown in FIG. 5. First, the specimen container 102 including specimen 212, which may be carried by carrier 122, is provided at the quality check module 130 in 502. Multiple images are captured at 504; the multiple images being multi-spectral images taken at multiple different exposures and at multiple different wavelength spectra and from multiple viewpoints, as described above. The multiple images may be stored in memory of the computer 143. From these images, the background may optionally be subtracted in a background reduction phase of 508 to lower computational burden. Background reduction may be accomplished by subtracting reference images previously taken in 510.

After image capture, and optional background reduction, segmentation is undertaken in 511. The segmentation in 511 may include an image consolidation process that is undertaken in 512. During this image consolidation process in 512, the various exposure time images at each color spectra (R, G, B, white light, NIR and/or IR) and for each camera 440A-4400 are reviewed pixel by pixel to determine those pixels that have been optimally exposed. For each corresponding pixel location, the best of any optimally-exposed pixel is selected and included in an optimally-exposed image data set. Thus, following image consolidation in 512, there is produced one optimally-exposed image data set for each spectrum and for each camera 440A-4400. The use of HDR processing may function to enrich the details of the images with respect to reflections and absorption.

Following image consolidation in 512 or possibly concurrent therewith, a statistics generation process may be undertaken in 514, where statistics are generated for each pixel, such as mean and/or covariance matrix. This statistical data on the optimally-exposed data sets are then operated on by a multi-class classifier 515 to provide identification of the pixel classes present in the images in 516. The final class for each pixel may be determined my maximizing confidence values for each pixel. For each pixel location, a statistical description may be extracted within a pixel (e.g., a small super-pixel patch (e.g. 11×11 pixels)). Each super-pixel patch provides a descriptor, which is considered in the training and evaluation process. Typically the classifiers operate on feature descriptors and use class labels for training and output class labels during testing/evaluation.

From this segmentation process of 511, each pixel in a consolidated image for each of the cameras 440A-440O is given a classification as one of a plurality of class types in 516. Class types may be liquid (serum or plasma portion 212SP), settled blood portion 212SB, tube 212T, label 218, cap 214, gel separator 313, air 212A, for example. From this segmentation information, the liquid area (the serum or plasma portion 212SP) may be determined in 518. This may involve identifying the location of the upper interface between liquid (serum or plasma portion 212SP) and air 212A (i.e., LA), SB, or the SPG (if a gel separator 313 is used), and the width (W). From this information, an estimate of the volume of the liquid region (the serum or plasma portion 212SP) may be determined. Once the liquid region is identified in 518, the presence of an interferent may be subsequently detected in 521. The presence of H, I, and/or L may take place by operating on the data subset of the liquid region (the serum or plasma portion 212SP) with one or more additional classifiers. In one embodiment, a separate classifier may be used for each of H, I, and L, as is described below.

Hemolysis Detection

According to first broad aspect, embodiments of the invention are directed at a method and apparatus that may be used to detect if the specimen 212 contained in a specimen container 102 of centrifuged blood is hemolyzed. The method utilizes multiple cameras 440A-440C, and multiple exposures (e.g., 4-8 exposures or more) and multiple wavelength spectra (e.g., R, G, B, near IR, and/or IR) for each camera to capture multiple pixelated images. These images are then analyzed and operated on to identify the liquid region in 518, as discussed above. This subset of data from the liquid region is further analyzed to identify hemolysis in 521H.

Hemolysis is a sample quality discoloration issue, and it cannot be resolved with special processing. Hemolysis (also spelled haemolysis) may occur when the red blood cells rupture and the hemoglobin inside is released into the serum or plasma portion 212SP of the specimen 212 that has been centrifuged. This gives the serum or plasma portion 212SP a reddish color or appearance. Along with a reddish color, potassium may be released into the serum or plasma portion 212S, which may give erroneous results when tested on an analyzer 106, 108, and/or 110. Incorrect blood collection, handling, storage, and/or processing may cause hemolysis.

The extent or degree of hemolysis may be characterized by a hemolytic index as determined in 526H. "Hemolytic index" as used herein shall mean a grade given to a particular specimen 212 based upon the determined content of hemolysis present in the serum or plasma portion 212SP. Generally, the grading scale for observation ranges from zero through four (0-4). Zero represents substantially no hemolysis while four represents significant hemolysis. Alternately, a scale of 0-10, 0-20, A-F, or a scale of some other range could be used. A specimen 212 having a sufficiently high hemolytic index, as determined by the quality check module 130, may be rejected. A usual procedure is to redraw another specimen 212 from the patient to ensure that a specimen 212 of good quality presented to the analyzer 106, 108, and/or 110. Thus, the specimen 212 exhibiting hemolysis may be rejected and offloaded at loading area 105 without being further tested. Optionally, the specimen 212 may be tested in an analyzer (e.g., analyzer 106, 108, or 110), and depending on the test ordered, the hemolysis index may be reported along with the test results.

Once a new specimen 212 is processed, and is deemed to be normal by quality check module 130, it may be successfully analyzed without the interfering hemoglobin. In some embodiments, if the specimen 212 is determined to contain hemolysis as detected at quality check module 130, the specimen 212 may be sent on to another analytical instrument (e.g., a specialized clinical analyzer at remote station 132—FIG. 1) where a precise level of hemolysis can be measured and characterized. An alert may be displayed on a display (e.g., computer screen) of the computer 143 or CIM 145 of the specimen testing apparatus 100 to alert lab personnel for further evaluation and/or decision making if the specimen 212 is found to contain hemolysis.

To improve an ability to convey the assessment of a specimen 212 containing hemolysis to laboratory personnel, an image of the specimen container 102 including the specimen 212 having hemolysis may be displayed on a display of the computer 143 or CIM 145. This image may be displayed along with other collaborative information such as, but not limited to, reference images of various known hemolyzed specimens, color spectra for comparison, the assessed level of hemolysis of the specimen 212 (i.e., the index), and/or suggested laboratory personnel action to take.

Icterus Detection

According to another broad aspect, embodiments of the invention are directed at a method and apparatus that may be used to detect icterus in a specimen 212 contained in a specimen container 102 of centrifuged blood. An icterus interferent may arise, for example, from an excess of bilirubin, the result of decaying red blood cells being converted into bilirubin in the spleen. Levels of bilirubin above 2-3 mg/dl are generally visibly dark yellowish or brownish in color and may adversely affect any enzyme-based immunoassays carried out on the analyzers (e.g., analyzers 106, 108, and/or 110). Such a condition is also termed bilirubinaemia.

The icterus detection method is similar to that for detecting hemolysis. After image capture and performing an analysis of the pixelated images to identify the liquid region in 518, the data subset from the liquid region may be analyzed for the presence of icterus. According to the method, the same digital image data subset that was used for the hemolysis detection may be used for icterus detection. The analysis may use a binary classifier to determine is icterus is present, and if so, may determine an interferent level, such as an icteric index. "Icteric index" as used herein shall mean the grade given to a particular specimen 212 based upon the determined content of icterus present. Generally, the grading scale for observation ranges from zero through four (0-4). Similarly, zero represents substantially no icterus, while four represents significant presence of icterus. Alternately, other scales could be used, such as 0-10, 0-20, A-F, or some other range.

Lipemia Detection

According to another broad aspect, embodiments of the invention are directed at a method and apparatus that may be used to detect lipemia in a specimen 212 contained in a specimen container 102 of centrifuged blood. A lipemia interferent, which may exhibit a whitish or milky appearance in the serum or plasma portion, may arise from the presence of excess lipids in the blood. Lipid levels above about 50 mg/dl may interfere with antibody binding in immunoassay testing and may accordingly affect an immunoassay result from the analyzer 106, 108, or 110.

The lipemia detection method is similar to that for detecting hemolysis and icterus. The method may receive the specimen container 102 in the quality check module 130. Next, cameras 440A-440C may capture pixelated images of the specimen 212. The computer 143 may then perform an analysis of the images to segment the specimen container 102 and specimen 212 in 511 and identify the liquid portion in 518. Finally, the image data subset may be analyzed for the presence of lipemia in 521L. According to the method, the same digital image data subset that was used for the hemolysis and icterus detection may be used for lipemia detection. The analysis may determine if an interferent is present, and if so, an interferent level, such as a lipemic index. "Lipemic index" as used herein shall mean the grade given to a specimen 212 based upon the determined content of lipemia therein. Generally, the grading scale for visual observation ranges from zero through four (0-4). Similarly, zero represents substantially no lipemia, while four represents significant presence of lipemia. Alternately, other scales could be used, such as 0-10, 0-20, A-F, or a scale of some other range. Lipemia is a specific sample quality discoloration defect, which may be resolved with special processing before the specimen 212 is tested or analyzed on an analyzer (e.g., analyzer 106, 108, and/or 110).

After the lab is aware the specimen is lipemic, they may further process the specimen 212, for example, at the remote station 132 to remove or reduce the lipids. For example, they may introduce a solvent or other material to reduce the amount of lipemia. Following the additional processing to lower the lipemia level at remote station 132, the specimen 212 can be returned to the track 121 and may be placed directly on an analyzer (e.g., analyzer 106, 108, and/or 110) for analysis. Optionally, the specimen 212 may again be routed to the quality check module 130 so to rescreen the specimen for lipemia. If the lipemia level is now sufficiently low, then the specimen may be routed on track 121 to be analyzed on the analyzer (e.g., analyzer 106, 108, and/or 110), and then return the specimen 212 to the loading area 105. With the retest for lipemia, the specimen 212 can be properly analyzed by one or more of the analyzers (e.g., analyzer 106, 108, 110) and the lab can be relatively more confident of the test results.

Thus, it should be apparent that embodiments of the invention may detect H, I, and/or L at the first possible instance (e.g., at the quality check module 130) after centrifugation of the specimen 212. By detecting H, I, and/or L at this point in the process, the specimen 212 will not be wasted, erroneous test results may be prevented, and any patient test result delay will be minimized. Of course, to provide an even more accurate measurement of the level of H, I, and/or L present in the serum or plasma portion 212SP, an artifact detection method may be employed to identify a presence of an artifact, such as clot, bubble, or foam. The pixels identified as containing one or more artifacts may be ignored in the method and not used for the HIL detection. The artifact detection method of 622 (FIG. 6) is further described in U.S. Provisional Patent Application No. 62/288,358 filed on Jan. 28, 2016, and entitled "Methods And Apparatus For Classifying An Artifact In A Specimen."

According to the method, the identifying hemolysis in 521H, identifying icterus in 521I, and identifying lipemia in 521L may be carried out by operating of the image data subset with one or more classifiers that are trained based on multiple training sets. Individual binary classifiers may be used for each of H, I and/or L, or even for N individually, or one multi-class classifier may be used for identifying any one or more of H, I, and/or L, that may be present or N. Optionally, the stored RGB values for each pixel of the data subset can be measured against RGB values in memory, such as in a lookup table.

In one or more embodiments, the determination of the presence of one or more interferent involves first analyzing the image data subset to characterize individual ones of the pixels as being either normal (N), or containing Hemolysis (H), Icterus (I) or Lipemia (L). From this determination, an overall classification of the liquid region may be provided. The overall classification may be as being normal (N) or including a particular type or types of interferent. For example, the particular interferent type(s) in the liquid region may be determined to be one of H, I, and/or L, such as H, I, L, H and I, H and L, I and L, or H, I, and L.

In one or more embodiments, the interferent classifier 521 may include any suitable supervised classification model. Interferent classifier 521 may utilize another classification model to determine whether the pixels that are classified as a being in the liquid region are one of the classes of N, H, I, or L. The interferent classifier in 521 may be based upon individual binary classifiers, one for each of H, I, and L, or on a multi-class classifier that has been sufficiently trained based on multiple interferent training sets for H, I, L, and N. In one embodiment, the multi-class classifier (e.g., a four class classification model) may be a support vector machine (SVM), support-vector network, or a boosting class algorithm. Examples of support vector machines and networks are described in a paper entitled "Support-vector Networks" by C. Cortes and V. Vapnik in Machine Learning Vol. 20, Issue 3, page 273-297, and in a paper entitled "Additive Logistic Regression: A Statistical View of Boosting" by J. Friedman, T. Hastie, R. Tibshirani (1998), and "A Short Introduction to Boosting" by Y. Freund and R. E. Schapire (1999).

Once the pixels of the image data subsets have been classified as being N, H, I, or L by the interferent classifier 521, the method 500 may include determining whether the liquid region of the specimen 212 is, as a whole, normal (N), or if not normal (N), containing one or more of H, I, and/or L. If the specimen 212 is deemed to be normal (N), then the specimen 212 simply progresses on the track 121 to an analyzer(s) (e.g., analyzer 106, 108, and/or 110) for which tests were ordered. If non-normal, then one or more interferent type is determined. Furthermore, an interferent level detector may be used, in 521B, to determine an interferent level of each interferent type.

The determination that the serum or plasma portion 212SP is, as a whole, normal (N), or if not normal (N), the interferent type, may be accomplished by adding a number of pixels in the liquid region that have been previously classified as being N, H, I, or L. The classification as normal (N) or as containing an interferent may be based upon a largest number of pixels in each class, or a weighting scheme in some embodiments. Thus, in one embodiment, if a majority of pixels are classified as N, then the liquid region and the specimen 212 may be categorized as normal (N). If a majority of pixels are classified as H, then the liquid region and the specimen 212 may be categorized as containing hemolysis (H). Likewise, if a majority of pixels are classified as I or L, then the liquid region and the specimen 212 may be categorized as Icterus (I), or lipemia (L), respectively. In other embodiments, a weighted majority voting scheme may be also used to classify the specimen 212 using probabilities from the interferent classifier 521 as a weight. Other means for characterizing the specimen 212, as a whole, may be used.

Moreover, if the image data set of the specimen 212 contains a relatively large amount of pixels that are classified in two or more interferent classes (e.g., H and I, H and L, I and L, or even H, I, and L), then the interferent detection method may report that multiple interferent types are present in the specimen 212. Once the specimen 212 has been given a characterization as containing multiple interferent types (e.g., H, I, and/or L), the interferent level detector 521B may be used to provide an interferent level for the multiple interferent types in the specimen 212. Interferent level detector 521B may obtain an interferent level or index for each particular interferent by passing the image data subset through a level characterizing model, such as a supervised regression model. Any suitable regression model may be used, such as support vector regression (SVR), neural network regression, tree-based regression, or the like.

A different regression model may be used for each interferent type, such as hemolysis regression model 526H, icterus regression model 526I, and lipemia regression model 526L. In one or more embodiments, each of the regression models may be an SVR machine and may be trained using only a liquid region that exhibits that particular type of interferent type (e.g., H, I, or L). For example, the hemolysis regression model 526H may be trained with a broad range of specimens 212 having hemolysis levels across a diverse range of expected hemolysis levels. For example, hemolysis ranges may include hemolysis levels from about 50-525. Likewise, the icterus regression model 526I may be trained with a broad range of specimens 212 having icterus levels across a diverse range of expected levels, including icterus levels from about 1.7 to 30. Similarly, lipemia regression model 526L may be trained with a broad range of specimens 212 having lipemia levels across a diverse range of expected levels, including lipemia levels from about 125-1,000.

In some embodiments, the interferent levels may be discretized. For example, four discreet levels may be used. For the hemolysis regression model 526H, discreet hemolysis levels of 50, 150, 250, and 525 may be used. For the icterus regression model 526I, discreet icterus levels of 1.7, 6.6, 16, and 30 may be used, and for the lipemia regression model 526L, discreet lipemia levels of 125, 250, 500, and 1,000 may be used. More or less than four discreet levels may be used. Levels other than the discreet levels listed above may be used.

Although the results from the multiple viewpoints may offer an indication of whether the specimen is normal (N) or contains on more of HIL, the final determination of the interferent level may be determined by fusing of the regression results of the image data subsets of that particular interference type as passed through the desired regression models. If the interference levels of the model have been discretized, then the output from the regression models will also be discretized by mapping to the closest target level. In any event, according to one or more embodiments, an interferent level or index may be provided for each detected interferent type in the specimen 212. The determinations may be aggregated according a weighted scheme where the images are weighted based upon the number of pixels of each class. The final decisions can be verified across the different views.

Accordingly, it should be apparent that the model-based interferent detection and classification method 500 carried out by the quality check module 130 may result in a rapid characterization of the specimen 212 as being either normal or containing one or more interferent therein. If the specimen 212 contains one or more interferent, then the method 500 may further determine the interferent type or types present, and may also determine an interferent level or index for each interferent type that is present. Final results and determinations can be aggregated across the multiple viewpoints.

Figure 6:
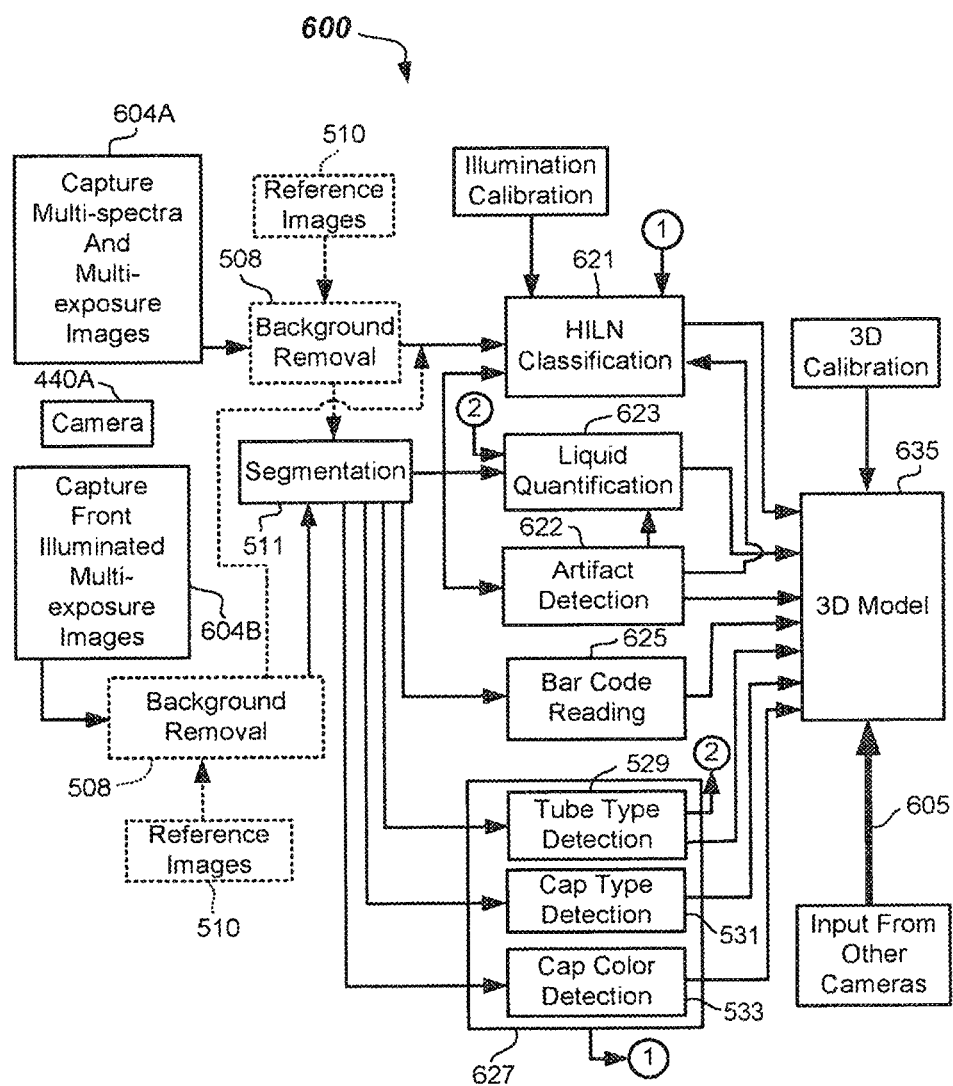
FIG. 6 illustrates a general block diagram of components of a specimen testing apparatus including a capability to determine a presence of an interferent in a specimen, as well as the capability to detect characteristics or quantify a specimen or a specimen container according to one or more embodiments.

FIG. 6 illustrates a flowchart of a broader characterization method 600 wherein the characterization of the interferent (i.e., HILN classification) in 621 is just one of the many items that may be characterized or classified by the broader method 600 using the quality check module 130. According to one or more embodiments of the method 600, images are captured, such as by multiple cameras (camera 440A is shown). However, other cameras 440B, 440C may be used to capture images from other viewpoints. The processing that will be described for the images captured on camera 440A is identical for the other cameras 440B, 440C at the other viewpoints and their inputs in line 605 may be used to develop a 3D model of the specimen 212 used for final determinations or resolving any differences in results as between the viewpoints.

The images captured by camera 440A and the other cameras 440B, 440C may be multi-spectral (e.g., RGB, near IR, IR) and multi-exposure images, as discussed above. In particular, multiple exposures (e.g., 4-8 exposures) may be taken for each wavelength spectrum of light used in 604A. The respective images at each exposure for each camera 440A-4400 may be obtained simultaneously using monochrome cameras and backlight light sources 444A-444C as described in FIGS. 4A-4B. Optionally, front illuminated multi-exposure images using a white light sources 444D-444F may be obtained in 604B using a color camera.

The images may then be optionally processed in 508 to remove background using reference images 510, as described above in optional background removal method. The images may then be further processed to determine segmentation in 511 in the manner described above. In some embodiments, the images from front lit cameras 440A-4400 (see FIGS. 4C-4D) from 604B may be best used for segmentation in 511. Likewise, any images captured in 604A using backlighting may be best used for characterization of HILN in 621. However, clearly, images captured in 604A could be used for segmentation in 511, and images captured in 604B could be used for HILN detection in 621.

Identifying and quantification of the liquid in 623 may also be carried out following segmentation in 511. Quantifying the liquid in 623 may involve the determination of certain physical dimensional characteristics of the specimen 212, such as a physical location of LA, SB, SG, and/or BG, and/or determination of HSP, HSB, and/or HTOT, and/or a volume of the serum or plasma portion (VSP) and/or a volume of the settled blood portion (VSB). The inner width (Wi) may be obtained from the specimen container characterization in 627. The identification may be accomplished by selecting the pixels at these demarcation areas and averaging their location values in pixel space to obtain a value for LA, SB or SPG. From this information, the volume of the serum or plasma portion 212SP may be determined. Correlation from pixel space to mechanical measurements may be accomplished by using any suitable calibration to calibrate pixels to millimeters.

To provide an even closer measurement of the actual volume of serum or plasma portion 212SP that is available for testing, an artifact detection method may be employed in 622 to identify a presence of clot, bubble, or foam. The respective estimated volume of the one or more artifacts present may be subtracted from the estimated volume of the serum or plasma portion 212SP determined above to obtain a better volume estimate. The images may then be processed using artifact classifiers to determine the presence or absence of an artifact in the serum or plasma portion 212SP in 622. Those pixels identified as an artifact by artifact detection 622 may then be ignored be the HILN classification in 621. Detection of an artifact may also initiate a remediation in some embodiments. Artifact detection method is described in U.S. Provisional Patent Application No. 62/288,358 filed on Jan. 28, 2016, and entitled "Methods And Apparatus For Classifying An Artifact In A Specimen."

The results of the segmentation in 511 can also be used to identify the label 218, which may include the identification information 215, such as a barcode. The barcode may be read in 625. Conventional barcode reading software may be used once the label 218 is identified in the segmentation in 511. If a particular image does not contain enough of the barcode to be read, the barcode can be read from, or in conjunction with the other images obtained from the other cameras 440A-440C.

Further characterization of the specimen container 102 may also be accomplished according to the broader method 600 in 627. The characterization of the tube type in 529, cap type in 531, and cap color in 533, may be fed to the 3D model 635 to verify that the same characterization was achieved based on processing the images from each camera 440A-440C. If slightly different values are obtained, then the values may be averaged. All of the outputs from the HILN classification in 621, liquid quantification in 623, artifact detection in 622, and specimen container detection in 627 may be fed into the 3D model 635, which may be used for final decision making, characterization, and harmonization of the results from the various cameras 440A-440C.

Figure 7:
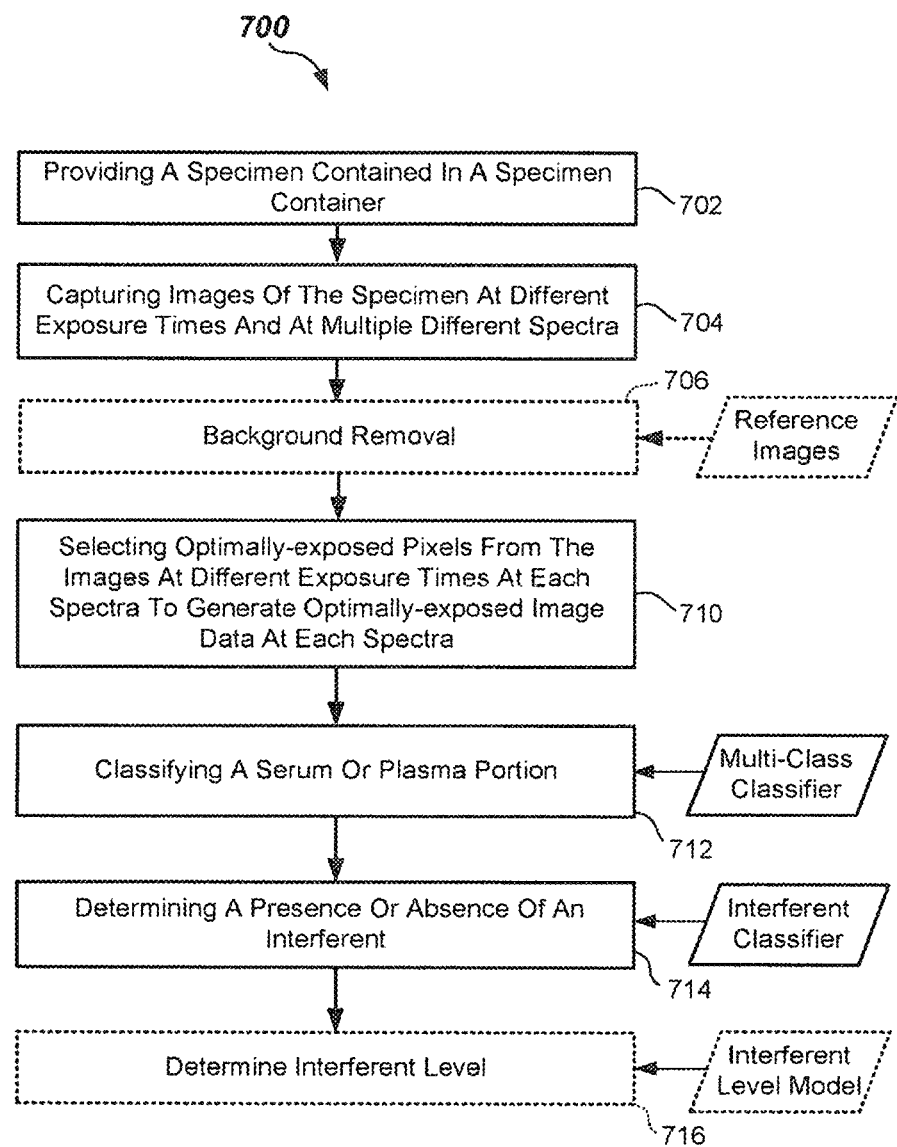
FIG. 7 is flowchart of a method of determining a presence of an interferent in a specimen according to one or more embodiments.

FIG. 7 illustrates a flowchart of a method of determining an interferent in a specimen 212 according to one or more embodiments of the disclosure. The method 700 includes providing a specimen (e.g., specimen 212) contained in a specimen container (e.g., specimen container 102, such as a capped, blood collection tube) in 702. Next, the method 700 includes capturing images of the specimen container 102 containing specimen 212 at different exposures times and at different spectra in 704. For example, there may be 4-8 different exposures or more taken at different exposure times in some embodiments, but under the same lighting conditions. In one or more embodiments, some images may be captured using white light and using front lighting, and some may be captured using a plurality of single-wavelength peak, narrow-band light sources, such as red, blue and green as backlit light sources 444A-444C. In other embodiments, NIR and/or IR spectral sources may be used. In some embodiment, white light images may be resolved into R, G, and B images as captured by the computer 143, as discussed above. In each instance, the images may be taken by multiple cameras 440A-440C from multiple viewpoints.

The method 700 may optionally include, as shown in 706, background reduction to subtract some of the background in order to lower computational burden. Background reduction may be accomplished by subtracting the images from corresponding reference images, which may be taken as part of a calibration process. Reference images may be taken at the same exposure times, wavelength spectra and lighting conditions as for the images of the specimen container 102, but may be captured without a specimen container 102 in the carrier 122. Background reduction phase may also include normalization.

The method 700 includes, in 710, selecting optimally-exposed pixels from the images at different exposure times at each wavelength to generate optimally-exposed image data at each wavelength spectra. For each corresponding pixel location in each image at a particular wavelength, the best exposed pixel (not under or over exposed) may be selected. The optimal exposure range may be as discussed above. This selecting optimally-exposed pixels takes place in an image consolidation phase (e.g., image consolidation 512). Thus, for each of the spectra (R, G, B, near IR, and/or IR), a data set of optimally-exposed pixels may be generated.

Next, the method 700 includes classifying the optimally-exposed pixels as being serum and plasma portion 212SP, i.e., the liquid region in 712. Classifying may be accomplished by computing statistical data of the optimally-exposed pixels at the different wavelength spectra to generate statistical data, and then operating on the statistical data of the optimally-exposed pixels to identify the serum and plasma portion 212SP. Other classes (e.g., settled blood portion 212SB, air 212A, tube 212T, label 218, and/or gel separator 313) may also be identified by the segmentation in 511.

Finally, the method 700 includes identifying the presence or absence of an interferent and an interferent type in 714 based on operating on the optimally-exposed exposed image data for each wavelength spectra with an interferent classifier. Optionally, in 716 an interferent level or index may be detected, such as by using an interferent level model such as a regression model or the like. Accordingly, based on the foregoing it should be apparent that a model-based specimen interferent detection method 700 carried out by the quality check module 130 may result in a rapid characterization of a presence of H, I, and/or L, or N. If an interferent is detected, an interferent level may be assessed and reported.

While the quality check module 130 has been shown in FIG. 1 as being located such that the pre-screening is performed immediately after centrifugation on the centrifuge 125, it may be advantageous to include this feature directly on an analyzer (e.g., analyzer 106, 108, and/or 110) in some embodiments, or elsewhere. For example, stand-alone quality check modules 130 located at remote station 132 that are not physically connected to the track 121 of the specimen testing apparatus 100 could use this technique to validate specimens 212 prior to analysis. Furthermore, in some embodiments, the centrifugation may be performed prior to loading the racks 104 into the loading area 105, so that in some embodiments, the quality check module 130 may be located at the loading area 105 and the quality check can be carried out as soon as the robot 124 loads a specimen container 102 into a carrier 122. Other locations for the quality check module 130 are possible.

While the invention is susceptible to various modifications and alternative forms, specific system and apparatus embodiments and methods thereof have been shown by way of example in the drawings and are described in detail herein. It should be understood, however, that it is not intended to limit the disclosure to the particular apparatus or methods disclosed but, to the contrary, the intention is to cover all modifications, equivalents, and alternatives falling within the scope of the appended claims.

What is claimed is:

1. A method of determining an interferent in a specimen contained within a specimen container, comprising:
   providing a specimen contained in a specimen container;
   providing two or more cameras;
   with each camera, capturing images of the specimen at varying exposure times and at multiple different spectra having different nominal wavelengths;
   selection of optimally-exposed pixels from the images at the varying exposure times at each of the spectra to generate optimally-exposed image data for each spectra;
   classifying a serum or plasma portion of the specimen; and
   determining whether an interferent is:
   present within the serum or plasma portion, or
   absent within the serum or plasma portion.

2. The method of claim 1, wherein the classifying the serum or plasma portion includes computing statistics of the optimally-exposed pixels at the different spectra to generate statistical data.

3. The method of claim 1, wherein the specimen is a centrifuged specimen including a separated blood portion and the serum or plasma portion.

4. The method of claim 1, wherein the capturing images of the specimen involves capturing multiple images with cameras from a number of different viewpoints.

5. The method of claim 4, wherein the number of viewpoints comprises 3 or more.

6. The method of claim 1, wherein the multiple different spectra comprise two or more spectra between about 400 nm and about 1500 nm.

7. The method of claim 1, wherein the multiple different spectra comprise two or more spectra between about 400 nm and about 700 nm.

8. The method of claim 1, wherein the multiple different spectra comprise red light, green light, blue light.

9. The method of claim 1, wherein the multiple different spectra comprise infrared and near infrared light.

10. The method of claim 1, wherein the varying exposure times comprise between about 0.1 ms and about 256 ms.

11. The method of claim 1, wherein the selection of optimally-exposed pixels comprises selection of pixels from the images that include intensities between 16-254 based upon a range of 0-255.

12. The method of claim 1, wherein the classifying the serum or plasma portion comprises using a multi-class classifier.

13. The method of claim 12, wherein the multi-class classifier comprises a support vector machine or a random decision tree.

14. The method of claim 1, wherein the determining a presence or absence of an interferent in the serum or plasma portion is based upon an interferent classifier generated from multiple training sets.

15. The method of claim 14, wherein the interferent classifier comprises a multi-class classifier capable of discerning hemolysis, icterus, and lipemia.

16. The method of claim 14, wherein the interferent classifier comprises individual binary classifiers capable of individually discerning hemolysis, icterus, and lipemia.

17. The method of claim 1, wherein selection of optimally-exposed pixels further comprises selecting a pixel having the highest intensity in response to more than one pixel being determined as optimally-exposed.

18. A quality check module adapted to determine presence of an interferent in a specimen contained within a specimen container, comprising:
- a plurality of cameras arranged around the specimen container and configured to capture multiple images of the specimen at varying exposure times and multiple spectra having different nominal wavelengths and from multiple viewpoints; and
- a computer coupled to the plurality of cameras and adapted to process image data of the multiple images, the computer configured to:
  - select optimally-exposed pixels from the multiple images at the varying exposure times for each spectra and generate optimally-exposed image data for each spectra,
  - classify a serum or plasma portion of the specimen, and
  - classify whether an interferent is:
    - present within the serum or plasma portion, or
    - absent within the serum or plasma portion.

19. The quality check module of claim 18 comprising a housing surrounding the specimen container received in a carrier, the carrier provided on a track.

20. The quality check module of claim 19 comprising an opening in a ceiling of the housing configured to allow specimen containers to be loaded into the quality check module from a top.

21. The quality check module of claim 18 comprising a plurality of RGB light sources providing back lighting.

22. The quality check module of claim 18 comprising a plurality of white light sources providing front lighting.

23. The quality check module of claim 18, wherein the computer is further configured and capable of being operated to select optimally-exposed pixels from the multiple images at the varying exposure times for each spectra and generate optimally-exposed image data for each spectra, wherein the optimally-exposed pixels comprise pixels greater than a minimum intensity and less a maximum intensity.

24. A specimen testing apparatus adapted to determine presence of an interferent in a specimen contained within a specimen container, comprising:
- a track;
- a carrier moveable on the track and configured to contain the specimen container;
- a plurality of cameras arranged around the track and configured to capture multiple images of the specimen at varying exposure times and multiple spectra including different nominal wavelengths and from multiple viewpoints; and
- a computer coupled to the plurality of cameras and configured to process image data from the multiple images, the computer configured to:
  - select optimally-exposed pixels from the multiple images at the varying exposure times and spectra to generate optimally-exposed image data for each spectra,
  - classify a serum or plasma portion of the specimen, and
  - classify whether an interferent is
    - present within the serum or plasma portion, or
    - absent within the serum or plasma portion.

* * * * *